United States Patent

Piesch et al.

[11] 3,966,769
[45] June 29, 1976

[54] SULFONYL COMPOUNDS

[75] Inventors: Steffen Piesch, Oberursel, Taunus; Friedrich Engelhardt, Frankfurt am Main, both of Germany

[73] Assignee: Cassella Farbwerke Mainkur Aktiengesellschaft, Germany

[22] Filed: Feb. 22, 1974

[21] Appl. No.: 444,810

Related U.S. Application Data

[62] Division of Ser. No. 259,201, June 2, 1972, Pat. No. 3,882,120.

[30] Foreign Application Priority Data

June 5, 1971  Germany............................ 2128011

[52] U.S. Cl. ............................................. 260/340.5
[51] Int. Cl.$^2$......................................... C07D 317/56
[58] Field of Search................................. 260/340.5

*Primary Examiner*—Lorraine A. Weinberger
*Assistant Examiner*—Michael Shippen
*Attorney, Agent, or Firm*—Connolly and Hutz

[57] ABSTRACT

Compounds of the formula $$R - SO_2 - X$$

wherein X is

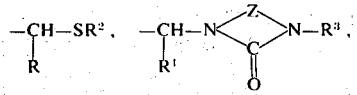

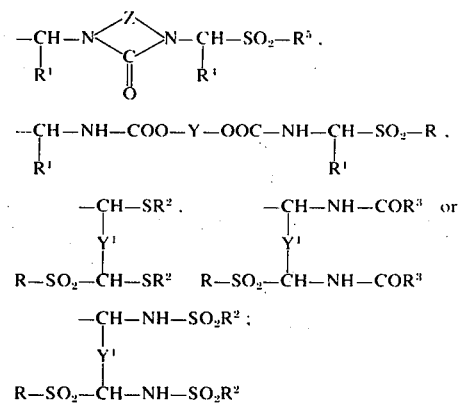

R and $R^5$ are aryl, aralkyl, heteroaryl, cycloalkyl or alkyl; $R^1$ and $R^4$ are R, hydrogen, carboxy or carboxylate; $R^2$ is aryl, aralkyl, cycloalkyl or alkyl; $R^3$ is $R^2$ or hydrogen; Y is alkylene, cycloalkylene or phenylene, $Y^1$ is Y or a direct bond and Z is alkylene, hydroxy substituted alkylene, alkylene interrupted by a hetero atom or

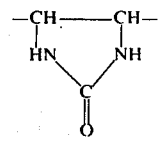

and methods of preparing the same.

2 Claims, No Drawings

SULFONYL COMPOUNDS

This is a division of application Ser. No. 259,201, filed June 2, 1972, now U.S. Pat. No. 3,882,120.

The present invention relates to sulfonyl compounds of the formula $$R - SO_2 - X \qquad I$$

wherein X is

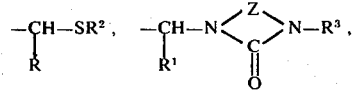

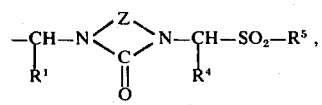

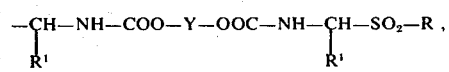

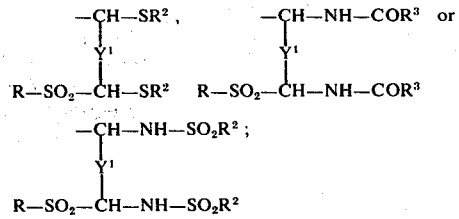

R and $R^5$ are phenyl, naphthyl, benzyl, phenethyl, thienyl, pyrrolyl, carbazolyl, pyridyl, phenothiazinyl, cycloalkyl having 4 to 8 carbon atoms, alkyl having 1 to 8 carbon atoms or one of said moieties substituted by alkyl, alkoxy, alkanoyl, alkanoyloxy or alkanoylamino having 1 to 4 carbon atoms or dialkylamino having 1 to 4 carbon atoms in each alkyl group, hydroxy, cyano, chlorine, fluorine, bromine, nitro, trifluoromethyl or carboxy;

$R^1$ and $R^4$ are R, hydrogen, carboxy or carboxylate;

$R^2$ is phenyl, naphthyl, benzyl, phenethyl, cycloalkyl having 4 to 8 carbon atoms, alkyl having 1 to 8 carbon atoms or one of said moieties substituted by alkyl, alkoxy, alkanoyl, alkanoyloxy or alkanoylamino having 1 to 4 carbon atoms or dialkylamino having 1 to 4 carbon atoms in each alkyl group, hydroxy, cyano, chlorine, fluorine, bromine, nitro, trifluoromethyl or carboxy;

$R^3$ is $R^2$ or hydrogen;

Y is alkylene having 1 to 8 carbon atoms, cycloalkylene having 4 to 8 carbon atoms or phenylene;

$Y^1$ is Y or a direct bond and

Z is alkylene having 2 to 3 carbon atoms, hydroxy substituted ethylene, —$CH_2$—O—$CH_2$— or

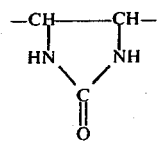

It will be understood by those skilled in the art that when one or more of the radicals $R^1$, $R^2$, $R^3$, $R^4$ and $R^5$ occur together with R in a given compound, the radical identities in said compound thereby defined may be the same or different. It will further be understood that when, for example, reference is made to alkyl, said alkyl may be straight-chained or branched.

Formula I embraces compounds of the following structures;

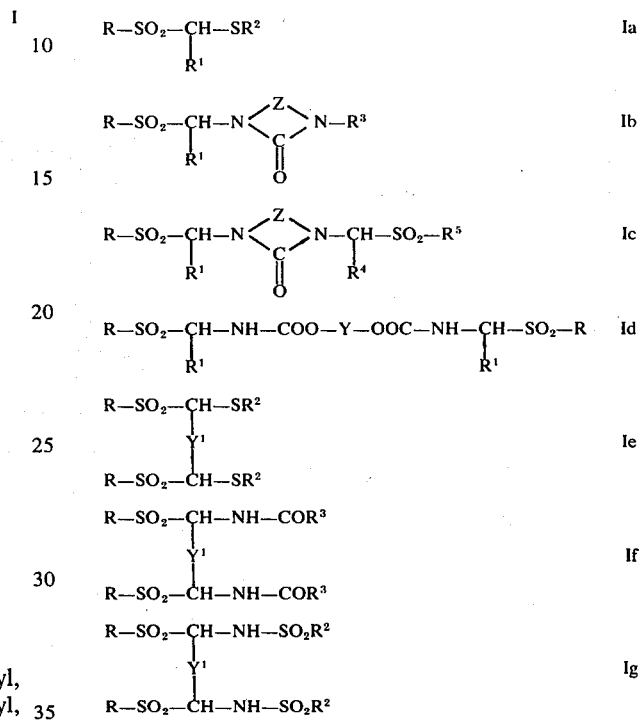

The novel compounds of this invention may be prepared in accordance with three different methods. These three methods are initially explained for the preparation of compounds of the formulae Ia and Ib as follows:

Method A

In this method, a sulfinic acid of the formula II or a salt of a sulfinic acid, preferably the sodium or potassium salt, is reacted with an aldehyde of the formula III in a suitable solvent to an oxysulfonyl compound of the formula IV:

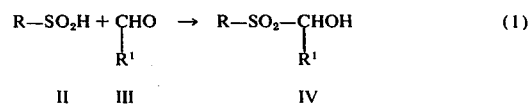

The oxysulfonyl compound of the formula IV is then, if required after its isolation, reacted with a compound of formula Va or Vb to obtain respectively Ia or Ib:

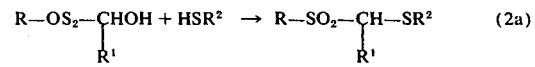

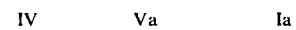

or

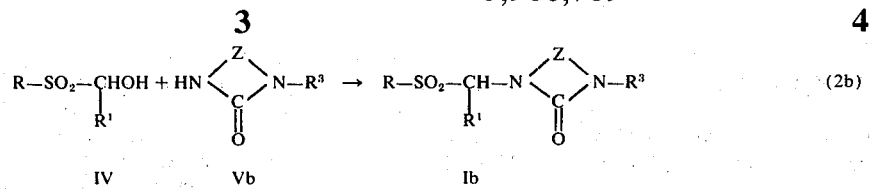

The oxysulfonyl compound of the formula IV is, as a rule, not particularly thermally stable so that it is generally advisable not to exceed a reaction temperature of 50°C.

Method B

A sulfinic acid of the formula II, an aldehyde of the formula III and a compound of the formula Va or Vb are simultaneously reacted in a suitable solvent:

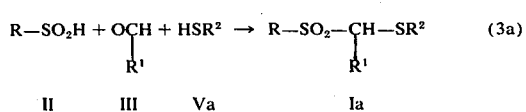

or

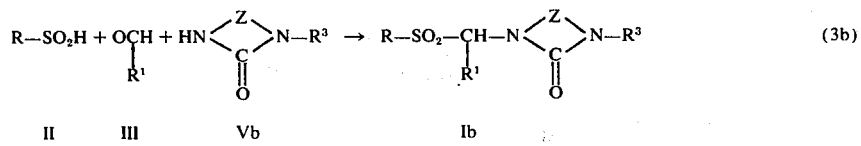

As solvents, there are preferably used glacial acetic acid, formic acid, alkanols having 1 to 4 carbon atoms, water, dimethylformamide, dimethylsulfoxide or solvent mixtures, particularly mixtures of the stated solvents. Normally, the three components are stirred in the solvent employed at temperatures between 5° and 100°C. The sulfinic acid may also be used in the form of a salt, e.g. its potassium or sodium salt. After some time, the novel compounds precipitate in the form of crystals. Upon their isolation, they may be recrystallized from a suitable solvent.

This process generally gives good yields. But in some instances, it proceeds unsatisfactorily, particularly when the reaction between the compound of the formula IV which is formed as an intermediate in this method and the compound of the formula Va or Vb proceeds so slowly that the compound of the formula IV decomposes at the reaction temperature.

Method C

In this method, a compound of the formula Va or Vb is first reacted with an aldehyde of the formula III to obtain a compound of the formula VIa or VIb:

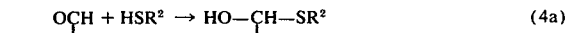

or

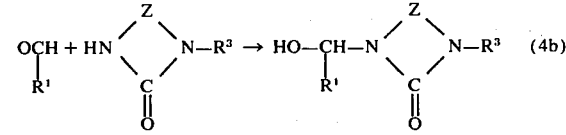

This reaction is also carried out in a suitable solvent or solvent mixture. Suitable solvents include water, glacial acetic acid, formic acid, ethylene chloride, dimethylformamide, dimethylsulfoxide, alkanols having 1 to 4 carbon atoms and mixtures thereof.

Rather drastic reaction requirements such as temperatures of up to 150°C and above, may be selected so that even compounds which are difficult to dissolve and/or slow to react of the formulae Va and Vb may be reacted.

Finally, the compound of the formula VIa or VIb, if required after its isolation, is reacted with a sulfinic acid of the formula II in a suitable solvent under mild reaction conditions:

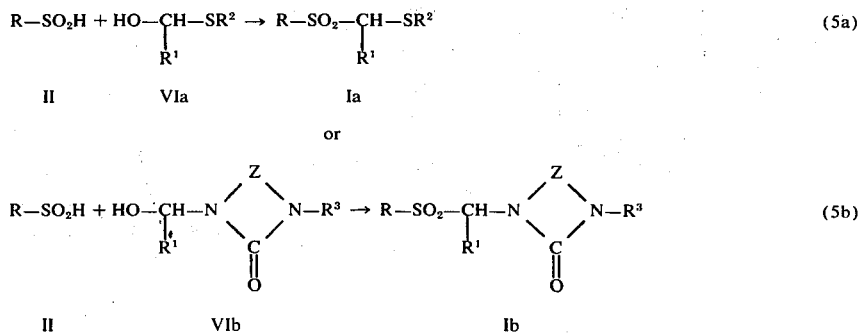

Solvents in this reaction include, for example, water, alkanols having 1 to 4 carbon atoms, formic acid, glacial acetic acid, dimethylformamide, dimethylsulfoxide and mixtures thereof.

The reaction temperatures for the reaction of the compounds VIa or VIb with the sulfinic acids are normally between 0° and 80°C.

Even with Method C, the sulfinic acid II may be used in the form of a salt. Moreover, in certain instances the aldehyde group may also be acetalized.

The novel compounds Ic to Ig may also be prepared according to the illustrated methods A, B and C. If, for example, with the three methods A, B or C, a compound wherein $R^3$ is H is used as a compound of the formula Vb, i.e., the compound Vc:

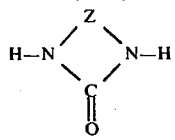

then one obtains as a final product a compound of the structure

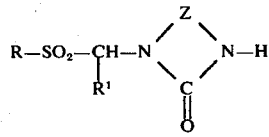

Ih

This compound may in turn be used with Methods A, B or C instead of compound Vb and yields, depending on the choice of aldehyde and sulfinic acid components, compounds of the formula:

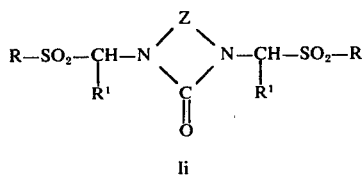

Ic

Of course, compounds o the formulae

Ik and

Il may also be prepared.

Symmetrical compounds of the formula I i may also be prepared according to Methods A and B when the reactions are carried out in the molar ratio of 2:1 and 2:2:1, respectively. The reaction equation of Method A then reads:

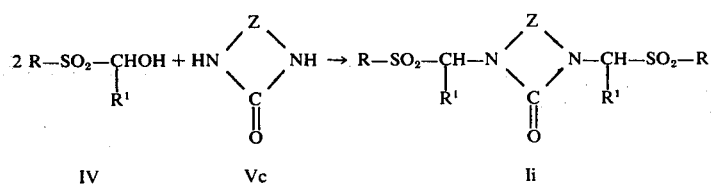   (2c)

The reaction equation of Method B then reads:

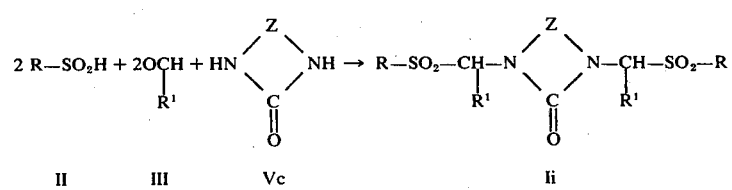   (3c)

If in the reaction equations 2c and 3c, the compound Vc is replaced by a compound of the formula Vd:

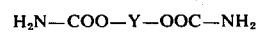

$H_2N—COO—Y—OOC—NH_2$ and if the remaining procedure is exactly the same as with Methods A and B, then compounds of the general formula I d are obtained.

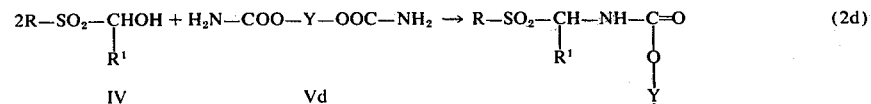   (2d)

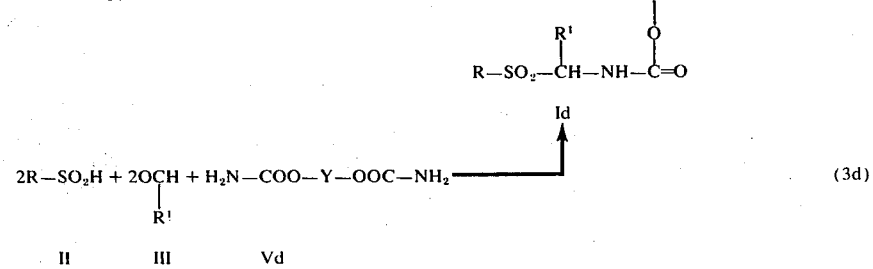   (3d)

If formaldehyde is used as aldehyde III with Methods A, B or C, then compounds are obtained wherein $R^1 = H$. Preferred novel compounds are those wherein $R^1 = COOH$. These are obtained when glyoxylic acid (OCH-COOH) is used as aldehyde III with Methods A, B or C.

Novel compounds of the formulae Ie, If and Ig are obtained when a dialdehyde IIIa is used as an aldehyde component with Methods A, B and C and if the molar ratios are changed accordingly. Method A then proceeds as follows:

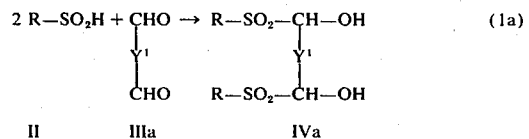

Q then stands for the residues $-NHCOR^3$, $-NHSO_2R^2$ and $-SR^2$. The reaction equation for Method B then reads:

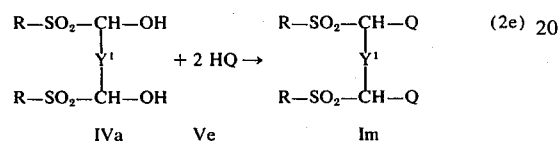

Method C, with the use of dialdehydes, proceeds as follows:

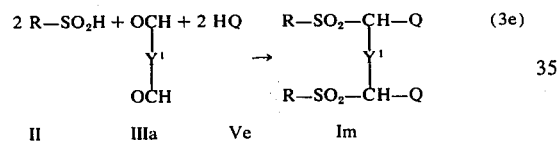

The statements made with respect to reaction conditions and solvents in Methods A, B and C also hold true for their modifications.

Examples of sulfinic acids of the formula II include methane-, ethane-, propane-, butane-, benzene-, p-toluene-, p-chlorobenzene-, 4-methoxybenzene-, 3-trifluoromethylbenzene-, 4-nitrobenzene-, 3-cyanobenzene-, 4-acetaminobenzene-, 3,4-dichloro-, 2,5-dichloro- or 2,6-dichlorobenzene-, 2,3,4-trichlorobenzene-, 2,5-dimethoxybenzene-, 3,4,5-trimethoxybenzene-, 2-methoxy-5-chlorobenzene-, 2-chloro-5-nitrobenzene-, 2-chloro-5-trifluoromethylbenzene-, 2-chloro-6-methylbenzene-, 4-hydroxy-5-carboxybenzene-, 2-thiophene- and 2-naphthalene-sulfinic acid.

As previously indicated, salts of the sulfinic acid, especially the sodium and potassium salts, may be used.

Sulfinic acids may, for example, be obtained either by reduction of the corresponding sulfonic acid chlorides (these again are obtainable by the reaction of the corresponding substituted benzenes with chlorosulfonic acid or from the corresponding substituted anilines by a modified Sandmeyer reaction according to Meerwein - Chem. Ber. 90, 841 (1957)) or by direct Sandmeyer reaction to the sulfinic acid. For example, the yet unknown 2-chloro-6-methylbenzene sulfinic acid (melting point: 110°C. with decomposition) was prepared from 2-chloro-6-methylaniline by way of 2-chloro-6-methyl-benzene sulfochloride (boiling point of 117°C. at 1.3mm). The preparation of sulfinic acids is summarized in Houben-Weyl, *Methoden der Organischen Chemie*, Vol. 9 (19), pp. 299 et. seq.

As aldehydes of the formual III, the following may be used, for example:
formaldehyde
acetaldehyde
propionaldehyde
n- or i-butyric aldehyde
n- or i-valeric aldehyde
caproic aldehyde
benzaldehyde
chloral
bromal
p-chlorobenzaldehyde
o-chlorobenzaldehyde
p-bromobenzaldehyde
p-methoxybenzaldehyde
o-methoxybenzaldehyde
3,4,5-trimethoxybenzaldehyde
o-hydroxybenzaldehyde 2,5-dichlorobenzaldehyde
3,4-dichlorobenzaldehyde
p-dimethylaminobenzaldehyde
p-acetylaminobenzaldehyde
tolylaldehyde
m-nitrobenzaldehyde
p-nitrobenzaldehyde
furfuraldehyde
furfural
acrolein
crotonaldehyde
pyridyl-3-aldehyde
glyoxylic acid (also in the form of its salts, particularly its sodium, potassium, calcium, ammonium, triethanolammonium and triethylammonium salt).

As dialdehydes of the formula IIIa, the following may be used, for example:
glyoxal
malondialdehyde
succinic dialdehyde
o-phthalaldehyde
isophthalaldehyde
terephthalaldehyde.

As thiols (mercaptans) of the formula Va, the following may be used, for example:

methane thiol
ethane thiol
propane thiol
butane thiol
β-hydroxyethane thiol
benzene thiol
p-chlorobenzene thiol
p-hydroxybenzene thiol
3,4-dichlorobenzene thiol
2-chloro-5-trifluoromethylbenzene thiol
3-trifluoromethylbenzene thiol
4-acetylaminobenzene thiol
4-dimethylaminobenzene thiol
2,3,4-trichlorobenzene thiol
4-bromobenzene thiol
2,5-dimethoxybenzene thiol
5-chloro-2-methoxybenzene thiol
1-naphthalene thiol
2-naphthalene thiol
2-chloro-6-methylbenzene thiol
4-methylbenzene thiol
phenylmethane thiol 3,4-dimethylbenzene thiol
cyclopentane thiol
p-mercaptobenzoic acid
mercapto acetic acid
mercapto acetic acid methylester
mercapto acetic acid ethylester
mercapto acetic acid propylester.

Thiols may be prepared in accordance with known per se processes, e.g., by alkylation or arylation of hydrogen sulfide and by the conversion of other sulfuric functions into the -SH group. In the alkylation of hydrogen sulfide, it is known to replace, for the sake of expedience, the second H atom by residues which may be easily removed again. For example, sodium thiosulfate, thiourea or xanthogenates are alkylated and the alkylation products converted into thiols by acidification or hydrolysis.

Aromatic thiols are advantageously prepared by the reduction of sulfonic acid chlorides.

Starting compounds of the formula Vb or Vc are cyclic urea or cyclic urea derivatives. There may be used, for example:

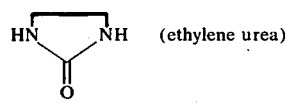 (ethylene urea)

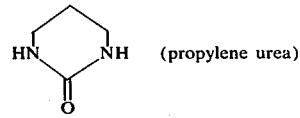 (propylene urea)

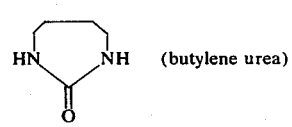 (butylene urea)

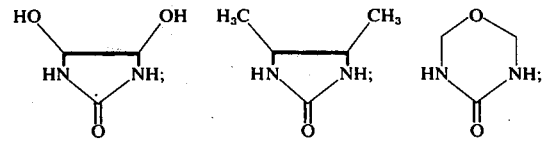

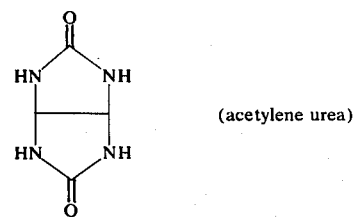 (acetylene urea)

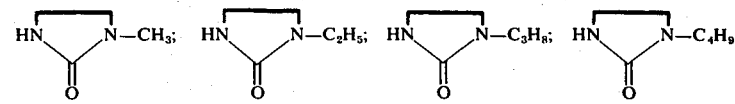

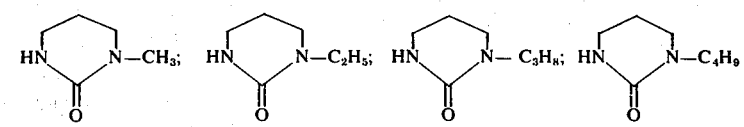

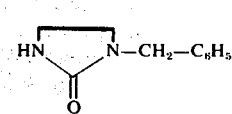

The non-creasing finishing agents in the trade are various methylolated cyclic ureas under the trade name Cassurit RI, Cassurit LR or Cassurit BFR, for example. Their structures, for example, are as follows:

p-trifluoromethylbenzamide
p-cyanobenzamide
o-chlorophenoxyacetamide
p-methoxphenoxyacetamide

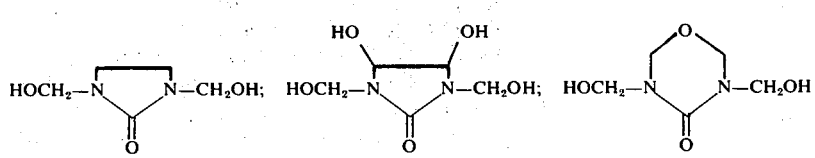

Such methylolated cyclic ureas may be directly reacted with a sulfinic acid according to Method C instead of the compounds VIa or VIb, e.g.:

phenoxyacetamide
2,5-dimethylphenoxyacetamide.

Carbonamides may be prepared easily, for example,

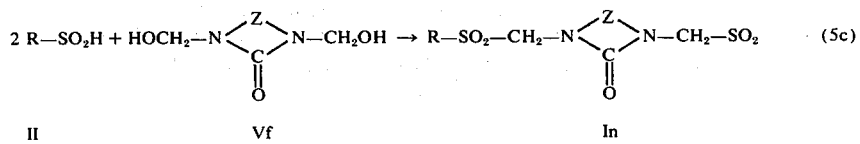

Starting compounds of the formula Vd may, for example, be obtained easily from urea and a diol VII according to the methods known for the preparation of urethanes:

by the reaction of the corresponding carbonic acid esters or acid chlorides with ammonia.

For the preparation of compounds of the formula Ig, sulfonamides, $H_2N-SO_2R^2$, are needed as starting

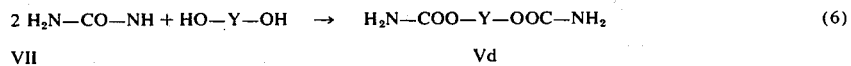

Used as diols, for example, may be:
glycol
1,3-propane diol
1,4-butane diol
1,5-pentane diol
1,6-hexane diol
neopentylglycol.

In the event Y is an aromatic intermediate member, corresponding compound Vd are suitably prepared as follows:

compounds. Suitable sulfonamides, for example, are:
methane sulfonamide
ethane sulfonamide
propane sulfonamide
butane sulfonamide
benzene sulfonamide
4-carboxybenzene sulfonamide
3-trifluoromethylbenzene sulfonamide
2,4-dimethoxybenzene sulfonamide
4-acetylaminobenzene sulfonamide

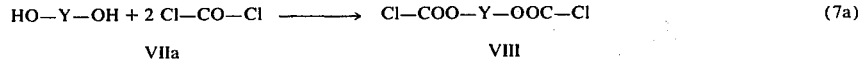

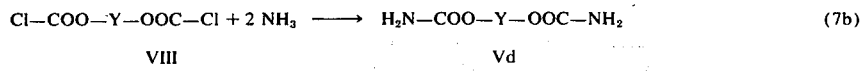

For the preparation of compounds of the formula If, carbonamides $H_2N-COR^3$ are needed as starting compounds. Suitable carbonamides, for example, are:
formamide
acetamide
propionamide
butyramide
trichloroacetamide
benzamide
p-tolylamide 2,3,4-trichlorobenzene sulfonamide
3-cyanobenzene sulfonamide.

So long as the novel compounds of the Formula I contain a carboxyl group, they can form salts with inorganic or organic bases. Of the inorganic salts, those with cations of the first or second main group of the Periodic Table are preferred. Ammonium, sodium, potassium, calcium and copper salts are particularly preferred. Of the salts with organic cations, those derived from trimethylamine, triethylamine, triethanolamine, morpholine, piperidine, pyrrolidine and aniline are preferred.

From the compounds containing carboxyl groups of the general formula I, the salts may be prepared in a manner known per se by reaction with inorganic or organic bases. In the preparation of alkali and earth alkali salts, particularly of the potassium, sodium and calcium salts, an alcoholate dissolved in alcohol is suitably used.

The compounds of formula I are particularly well suitable as reducing component in Redox-catalyst systems used for the production of homo and copolymers of olifinic compounds.

Oxidizing components of the Redox-catalyst system include, as customary, air and organic as well as mineral peroxy compounds, such as benzoylperoxide, tert.-butylhydroperoxide, di-tertiary-butyl peroxide, lauroyl peroxide, cumol hydroperoxide, acetyl peroxide, methylethylketone peroxide, hydrogen peroxide, potassium peroxide disulfate and ammonium peroxide disulfate.

Suitable monomers which may be polymerized with Redox-catalysts containing as reducing components compounds of the present invention are, for instance: acrylic acid, methacrylic acid as well as the salts thereof, esters and amides, methylolacrylamide or methacrylamide and their reaction products with amines and alcohols, vinylpyrrolidone, vinylcarbazole, vinylmethyl ketone, acrylnitrile, vinylidene cyanide, esters of unsaturated alcohols, such as vinylacetate and dialkylphthalate. For the preparation of copolymers with the monomers already known there may also be used styrene, α-methyl-styrene, vinyltoluene, halogeno-styrenes, for example, 2,5-dichloro-styrene and allylbenzene.

The polymerization can be effected as precipitation, emulsion, solution and bulk polymerization.

Particularly favorable results are achieved in the case of the homo and copolymers of the acrylamide in an aqueous solution. In this respect, specially those instant compounds are valuable as components for the Redox-catalyst system which contain a carboxyl group and, hence, dissolve in aqueous solutions or solutions of weak alkalies, such as bicarbonate or sodium carbonate solution.

The polymerization is performed in a manner known per se under atmospheric pressure and at temperatures ranging between 0° – 120°C., preferably between 20° – 70°C. The concentration of the instant compound which acts as reducing component of the Redox-catalyst system is normally appr. 0.02 to 1.5 per cent by weight, related to the weight of the monomer or mixture of monomers to be polymerized. The concentration of the oxidizing component of the Redox-catalyst system is normally between about 0.25 and 2.0 per cent by weight, likewise related to the weight of the monomer or the mixture of monomers to be polymerized.

The homopolymers manufactured by using the named Redox-catalyst systems, which contain as reducing component a compound of the present invention, distinguish themselves by a better water-solubility and a more even distribution of the molecular weight than by using known Redox-catalyst systems.

As compared to the known Redox-catalyst systems, the use of the Redox-catalyst systems, which contain as reducing component a compound of the present invention, additionally results in a substantially better and more even course of polymerization because in the event of more favorable monomer conversions the polymerization runs at lower temperatures.

In the following examples, "(Z)" means with decomposition. Additionally, when "-" is used in the tabulation in connection with the definition of $Y^1$, this has reference to a direct bond.

EXAMPLE 1 (Method A)

The sodium salt of p-toluenesulfinic acid (35 g), 200 ml. water, 30 ml 85% formic acid and 20 ml 39% formaldehyde are stirred in water for 3 hours at 40°C. Then 16 g ethylene urea are added to the clear solution and it is stirred for an additional 10 minutes at 40°C. and for another 2 hours at 10°C. About 10 minutes after the addition of ethylene urea, the product begins to crystallize into colorless needles.

There are obtained 38.5 g. (76% of the theoretical) of the compound:

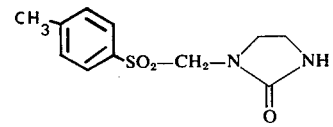

having a melting point of 158°C. (Z).

EXAMPLE 2 (Method B)

The soduum salt of 3,4-dichlorobenzene sulfinic acid (24 g), 10 g ethylene urea, 75 ml water, 200 ml 85% formic acid and 15 g o-chlorobenzaldehyde are dissolved while stirring at 40°C. until the solution becomes clear. After 5 minutes, crystallization begins. Stirring is continued for one-half hour at 40°C., the mixture is cooled to 10°C. and subjected to vacuum. The product is washed with water. It may be recrystallized from isopropanol.

Yield: 32 g (77% of the theoretical) of the compound:

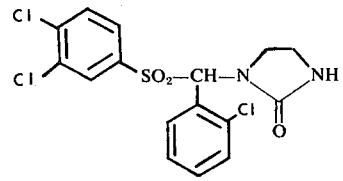

having a melting point of 161°C.

EXAMPLE 3 (Method C)

Propylene urea (10 g), 40 g glyoxylic acid (40% aqueous), 20 ml water and 10 ml 85% formic acid are stirred for 3 hours at 80°–85°C. This is then cooled to 40°C. and a solution of 40 g of the sodium salt of p-toluene sulfinic acid in 150 ml water and 50 ml 85% formic acid is added at once. This is stirred for 5 hours at 40°C. and then 15 ml 25% hydrochloric acid is added. It is cooled to 10°C. After standing overnight, the product is crystallized out. It is drawn off and washed with 100 ml ice water. The product may be recrystallized from isopropanol.

Yield: 30 g (58% of the theoretical) of the compound:

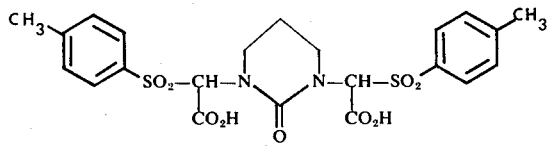

It readily dissolves in aqueous sodium hydrogen carbonate solution.

EXAMPLE 4 (Method C)

The sodium salt of 3,4-dichlorobenzene sulfinic acid (25 g), 50 ml water, 50 ml 85% formic acid and 15 g Cassurit RI (dihydroxymethylethylene urea, 50% in water) are stirred for 3 hours at 50°C. Crystallization begins after 20 minutes. Upon cooling to 10°C. and standing overnight, the colorless needles of the compound:

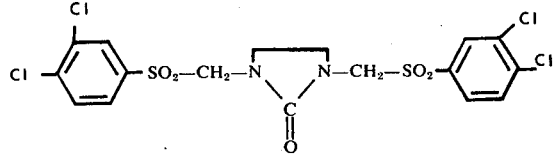

having a melting point of 210°C. (Z) are drawn off and washed well with water. Recrystallization may be from dioxane.

Yield: 22.6 g (87% of the theoretical).

The following compounds are prepared analogously:

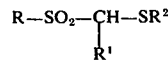

| R | R$^1$ | R$^2$ | Melting Point - °C. | Method |
|---|---|---|---|---|
| CH$_3$-C$_6$H$_4$- | (benzodioxole) | —CH$_2$CH$_2$OH | 102° | C |
| CH$_3$-C$_6$H$_4$- | -C$_6$H$_4$-OCH$_3$ | —CH$_2$CH$_2$OH | 102° | A, C |

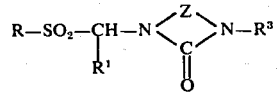

| R | R$^1$ | Z | R$^3$ | Melting Point - °C | Method |
|---|---|---|---|---|---|
| 2-Cl, 6-CH$_3$-C$_6$H$_3$- | H | —CH$_2$—CH$_2$— | H | 188° | B |
| 4-Cl, 2-OCH$_3$-C$_6$H$_3$- | H | —CH$_2$—CH$_2$— | H | 190° | B |

-continued

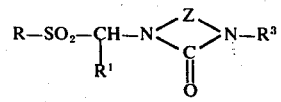

| R | R¹ | Z | R³ | Melting Point - °C | Method |
|---|----|---|----|--------------------|--------|
| 2,4-dichlorophenyl | H | —CH₂—CH₂— | H | 116° | B |
| 4-chlorophenyl | H | —CH₂—CH₂— | H | 148° | B |
| 4-methylphenyl | H | —CH₂—CH₂— | H | 158° | B |
| 3,4-dichlorophenyl | 2-chlorophenyl | —CH₂—CH₂— | H | 161° | B |
| 4-chloro-2-methoxyphenyl | 3-methoxyphenyl | —CH₂—CH₂— | H | 150° | B |
| 4-chloro-2-methoxyphenyl | 4-methoxyphenyl | —CH₂—CH₂— | H | 148° | B |

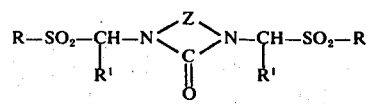

| R | R¹ | Z | Melting Point - °C | Method |
|---|----|---|--------------------|--------|
| 4-methylphenyl | H | —CH₂—O—CH₂— | 160° (Z) | C |
| 4-chlorophenyl | 2-chlorophenyl | —CH₂—CH₂— | 175° (Z) | C |
| 4-chloro-3-nitrophenyl | H | —CH₂—CH₂— | 180° (Z) | C |

-continued
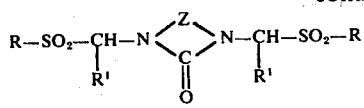
| R | R¹ | Z | Melting Point - °C | Method |
|---|---|---|---|---|
|  | | | | |
| | —CO₂H | —CH₂—CH₂—CH₂— | 127° (Z) | C |
| 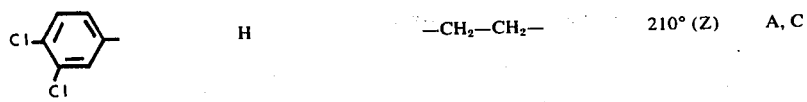 | H | —CH₂—CH₂— | 210° (Z) | A, C |
| 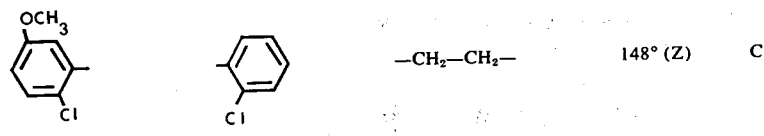 | | —CH₂—CH₂— | 148° (Z) | C |
|  | H | —CH₂—CH₂— | 206° | C |
| 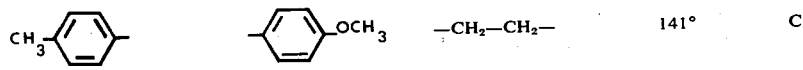 | | —CH₂—CH₂— | 141° | C |
|  | | —CH₂—CH₂— | 150° (Z) | C |
| 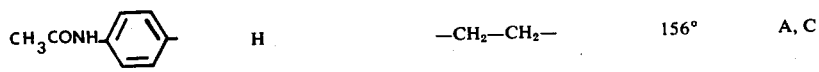 | H | —CH₂—CH₂— | 156° | A, C |
| 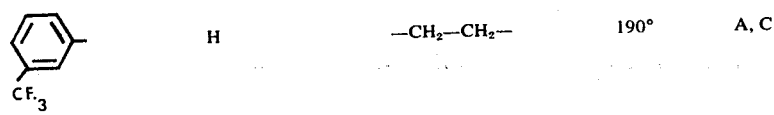 | H | —CH₂—CH₂— | 190° | A, C |
| 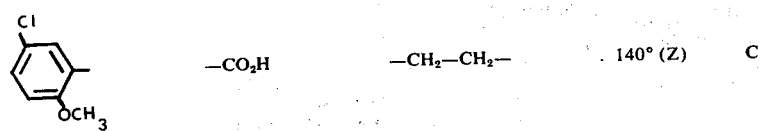 | —CO₂H | —CH₂—CH₂— | 140° (Z) | C |
| 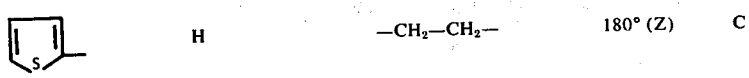 | H | —CH₂—CH₂— | 180° (Z) | C |
| 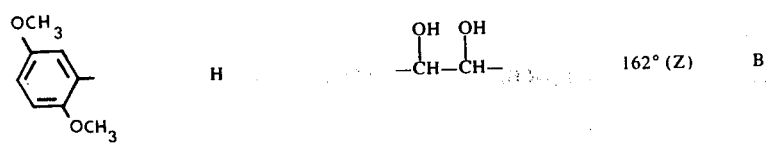 | H | —CH—CH— with OH OH | 162° (Z) | B |

-continued

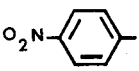

| R | R¹ | Z | Melting Point - °C | Method |
|---|----|---|-------------------|--------|
| $O_2N$-C₆H₄- | H | $-CH_2-CH_2-$ | 190° (Z) | C |

$$R-SO_2-CH(R^1)-NH-COO-Y-OOC-NH-CH(R^1)-SO_2R$$

| R | R¹ | Y | Melting Point - °C | Method |
|---|----|---|-------------------|--------|
| $CH_3$-C₆H₄- | -C₆H₄-$CH_3$ | $-(CH_2)_2-$ | 174° (Z) | C |
| $CH_3$-C₆H₄- | H | $-CH_2-C(CH_3)_2-CH_2-$ | 180° (Z) | C |
| Cl-C₆H₄- | H | $-(CH_2)_6-$ | 140° (Z) | C |
| $CH_3$-C₆H₄- | H | $-(CH_2)_6-$ | 163° (Z) | C |
| Cl-C₆H₄- | 2-Cl-C₆H₄- | $-CH_2-CH_2-$ | 154° | C |

$$\begin{array}{c} R-SO_2-CH-NH-SO_2-R^2 \\ | \\ Y^1 \\ | \\ R-SO_2-CH-NH-SO_2-R^2 \end{array}$$

| R | Y¹ | R² | Melting Point - °C | Method |
|---|----|----|--------------------|--------|
| $H_3C$-C₆H₄- | — | C₆H₄-Cl | 160° (Z) | B |
| 2,5-(OCH₃)(H₃CO)-C₆H₃- | — | C₆H₄-Cl | 148° (Z) | B |
| 3-$F_3C$-C₆H₄- | C₆H₄- | $CH_3$ | 174° (Z) | C |

-continued

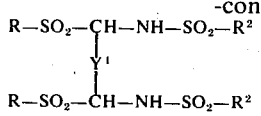

| R | Y¹ | R² | Melting Point - °C | Method |
|---|---|---|---|---|
| 3,4-dichlorophenyl | —CH₂— | 4-(NHCOCH₃)phenyl | 164° (Z) | C |
| 3-cyanophenyl | —CH₂— | phenyl | 125° (Z) | C |
| 4-nitrophenyl | — | 2,4-dimethoxyphenyl | 144° (Z) | A |
| 2-CF₃-3-Cl-phenyl | —CH₂CH₂— | 3,4-dichlorophenyl | 180° (Z) | B |
| 4-(CH₃CONH)phenyl | phenyl (1,3-) | —CH₃ | 154° (Z) | C |
| 2-thienyl | — | 2-CF₃-phenyl | 178° (Z) | C |
| phenyl | —CH₂— | 2-naphthyl | 190° (Z) | C |
| 5-(N,N-dimethylamino)-1-naphthyl | — | 4-methylphenyl | 140° (Z) | A, C |

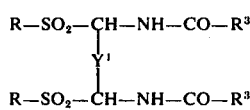

| R | Y¹ | R³ | Melting Point - °C | Method |
|---|---|---|---|---|
| 4-methylphenyl | — | phenyl | 200° (Z) | C |
| 4-nitrophenyl | —CH₂— | —CH₃ | 210° (Z) | C |

-continued $$R-SO_2-\underset{\underset{R-SO_2-CH-NH-CO-R^3}{Y^1}}{CH}-NH-CO-R^3$$

| R | Y¹ | R³ | Melting Point - °C | Method |
|---|---|---|---|---|
| 2-chloro-3-methylphenyl | — | —C₂H₅ | 177° (Z) | C |
| 2,3,6-trichlorophenyl | — | —CH₃ | 220° (Z) | C |
| 3-(trifluoromethyl)phenyl | —CH₂—CH₂— | —CH₂—C₆H₄—OCH₃ (p) | 160° (Z) | C |
| 4-chlorophenyl | —C₆H₄— (p) | —CH₃ | 217° (Z) | A |
| 2,5-dimethoxyphenyl | —C₆H₄— (p) | —CH₃ | 197° (Z) | A |
| 2-naphthyl | —CH₂— | 3,4,5-trimethoxyphenyl | 184° (Z) | A |
| 2-thienyl | — | —CCl₃ | 159° (Z) | C |
| 4-chloro-2-methoxyphenyl | — | —CH₂—C₆H₄—Cl (p) | 190° (Z) | C |
| 3-cyanophenyl | —CH₂CH₂— | —CH₃ | 205° (Z) | B |

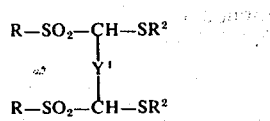
| R | Y¹ | R² | Melting Point - °C | Method |
|---|---|---|---|---|
| H₃C–C₆H₄– | — | –CH₂CH₂OH | 127° (Z) | B |
| O₂N–C₆H₄– | –C₆H₄– | –CH₂CH₂OH | 170° (Z) | B |
| 4-Cl-3-O₂N-C₆H₃– | –CH₂– | –CH₂–CO–OCH₃ | 157° (Z) | C |
| CH₃–CO–NH–C₆H₄– | | –C₆H₄–Cl | 170° (Z) | C |
| 3-F₃C–C₆H₄– | — | 2,5-(OCH₃)₂–C₆H₃– | 194° (Z) | C |
| 3-NC–C₆H₄– | –CH₂CH₂– | –C₆H₅ | 162° (Z) | C |
| 4-Cl-2-OCH₃–C₆H₃– | — | –CH₂CH₂OH | 124° (Z) | C, B |
| 2-thienyl– | –CH₂– | –C₄H₉(n) | 110° | C |
| 2-naphthyl– | — | –CH₂CH₂OH | 145° (Z) | C |
| 2,3,4-Cl₃–C₆H₂– | –C₆H₄– | –C₂H₅ | 205° (Z) | C |
| C₆H₅– | — | 2,3-Cl₂–C₆H₃– | 200° (Z) | B, C |

-continued $$R-SO_2-\underset{\underset{R-SO_2-\overset{|}{C}H-SR^2}{\overset{|}{Y^1}}}{\overset{|}{C}H-SR^2}$$

| R | $Y^1$ | $R^2$ | Melting Point - °C | Method |
|---|---|---|---|---|
| 2,4-Cl₂C₆H₃- | — | C₆H₅- (H) | 135° (Z) | C |

EXAMPLE 5

Into a glass polymerization vessel equipped with stirrer, thermometer, reflux cooler and dropping funnel is placed a mixture of 90 g n-butanol, 30 g butylacrylate, 10 g ethylacrylate, 20 g styrene, 12 g acrylic acid and 10 g hydroxypropylmethacrylate. While stirring, there are added 2 g of a compound of the formula

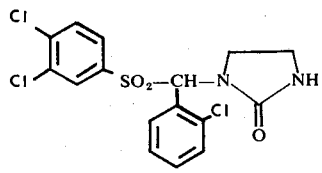

having a melting point of 161°C. dissolved in dimethylsulfoxide, 0.1 g dibutylaminohydrochloride as well as 1 ml of an alcoholic solution of copper acetylacetonate (0.1 ml solution corresponds to 12.3 γ Cu⁺⁺).

Once the air is displaced by nitrogen, the mixture is heated to 80°C. and within 2 hours a solution consisting of 2 g tert. butyl hydroperoxide (70%), dissolved in 10 ml n-butanol is added dropwise. After another 6 hours, polymerization is complete. The clear polymeric solution obtained contains 49.5% polymer and has a viscosity of 4600 centipoise.

EXAMPLE 6

Acrylamide (250 g) is dissolved in a mixture of 750 ml water (deionized) and 0.85 g 50% NaOH. While introducing nitrogen to this solution, there are added 0.5 g dibutylamine hydrochloride, 0.25 ml of a copper acetylacetonate solution (1 g solution corresponds to 12.3γCu⁺⁺), 0.25 g of the compound

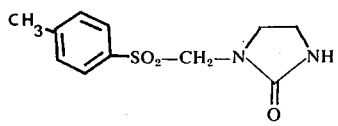

having a melting point of 158°C. (Z). dissolved in 5 ml dimethylsulfoxide and 0.25 g ammonium peroxy disulfate.

The catalyzed reaction mixture, which is adjusted to a temperature of 20°C., is transferred to a container of polyethylene. After about 1½ hours, polymerization begins and the temperature of the polymerization mixture rises to 90°–92°C.

There is obtained a non-flowable, polymeric gel which, after being reduced to small pieces, and, if necessary, after being dried and milled, is completely dissolved in water. The resulting highly viscous polymer solution is excellently suitable as a flocculating agent.

EXAMPLE 7

A polyester is prepared in the following way:
30 g. 1.2 propylene glycol
23 g. maleic acid anhydride
17 g. phthalic acid anhydride
are condensed at a temperature of 180°–190°C. for eight hours in the presence of a trace of hydroquinone. Then the whole is cooled to 120°C. and 30 g. methylmethacrylate are introduced while stirring. After further colling down to room temperature, the said polyester is obtained having an acid number of 18 and an OH number of 20. Of this polyester there are introduced 15 g. into a beaker and 0.5 g. of the catalyst

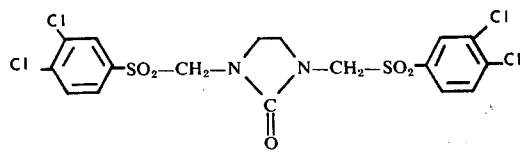

dissolved in 1,3 ml dimethylformamide, and as an accelerator solution, 0.5 ml commercial octa-soligen-cobalt-6-solution with 6% cobalt are stirred in. Subsequently a 2.0 mm thick layer is applied onto a glass plate. The layer thus obtained is completely polymerized in about 1¾ hours and is non-tacky.

In comparison thereto, polymerization with benzoylperoxide and octa-soligen-cobalt-6-solution requires about 5 days to yield a non-tacky surface.

EXAMPLE 8

In a polymerization vessel equipped with stirrer, reflux cooler, 2 inlets and a water bath, a mixture of 100 g acrylonitrile, 1200 ml deionized water and 1.0 ml aqueous 0.01% CuSO₄ solution is introduced. After displacing the air by the introduction of nitrogen, there are added 1 g NaCl as well as 1.0 g of a compound of the formula

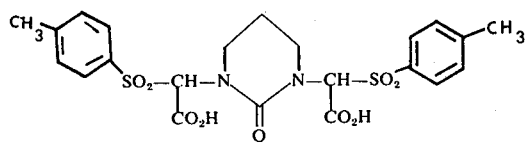

The temperature of the mixture is then brought to 50°C. Then a 0.5% aqueous solution of $K_2S_2O_8$ is added dropwise. As soon as the reaction is started (about 10 minutes) and the temperature has risen to about 55°–58°C. in the reaction mixture, further acrylonitrile is allowed to flow in from the storage vessel in such a manner that the reaction temperature is maintained between 57° and 60°C. In this manner, in the course of about 1½ hours, 150 ml potassium peroxy disulfate solution and 100 ml acrylonitrile are supplied. Upon completing polymerization, stirring is continued for another hour at 65°C.

The polymer obtained is filtered off and dried. It has a K-value of 86.7 measured in dimethylformamide.

We claim:

1. A compound of the formula

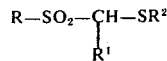

wherein R is phenyl, naphthyl, benzyl or phenethyl or one of said moieties substituted on the aromatic moiety thereof by alkyl having 1 to 4 carbon atoms, hydroxy, chlorine, bromine, fluorine, nitro or trifluoromethyl; $R^1$ is phenyl, naphthyl, benzyl or phenethyl substituted on the aromatic moiety thereof by methylenedioxy and $R^2$ is alkyl having 1 to 8 carbon atoms substituted by hydroxy.

2. The compound:

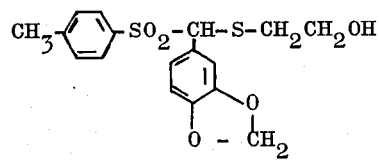

* * * * *